United States Patent
Willing

(10) Patent No.: US 7,655,102 B2
(45) Date of Patent: Feb. 2, 2010

(54) METHOD FOR THE APPLICATION OF REUSABLE FASTENERS ON DIAPERS

(75) Inventor: Christoph Willing, Vreden (DE)

(73) Assignee: Nordenia Deutschland Gronau GmbH, Gronau (DE)

( * ) Notice: Subject to any disclaimer, the term of this patent is extended or adjusted under 35 U.S.C. 154(b) by 0 days.

(21) Appl. No.: 10/573,640

(22) PCT Filed: Sep. 24, 2004

(86) PCT No.: PCT/EP2004/010775

§ 371 (c)(1),
(2), (4) Date: May 3, 2006

(87) PCT Pub. No.: WO2005/030104

PCT Pub. Date: Apr. 7, 2005

(65) Prior Publication Data

US 2006/0237116 A1  Oct. 26, 2006

(30) Foreign Application Priority Data

Sep. 25, 2003  (DE) .............................. 103 44 536

(51) Int. Cl.
*B32B 37/00*  (2006.01)
(52) U.S. Cl. .................... 156/73.1; 156/265; 156/308.2
(58) Field of Classification Search ............ 156/73.129, 156/297, 299, 308.2, 308.4, 580.1, 580.2, 156/581, 582, 583.1, 256, 265, 73.1, 290
See application file for complete search history.

(56) References Cited

U.S. PATENT DOCUMENTS 5,261,997 A * 11/1993 Inselmann ................ 156/556
6,471,804 B1  10/2002 Tennby et al.

FOREIGN PATENT DOCUMENTS

| DE | 197 03 557 A1 | 9/1997 |
|---|---|---|
| DE | 199 40 185 A1 | 4/2000 |
| DE | 199 52 417 A1 | 5/2001 |
| EP | 0 877 589 B1 | 1/1997 |
| EP | 0 793 953 A | 9/1997 |
| EP | 0 818 188 A | 1/1998 |

OTHER PUBLICATIONS

International Search Report.

* cited by examiner

*Primary Examiner*—James Sells
(74) *Attorney, Agent, or Firm*—Collard & Roe, P.C.

(57) ABSTRACT

The invention relates to a method for the application of a reusable fastener, comprising a sealing band and a sealing strip, to a diaper. According to the invention, strips, comprising a support and a backed material with sealing elements in the form of loops or hooks, are fixed to the diaper without adhesive. In a first method step the strips are attached by means of thermobonding or ultrasound welding. In a second methods step, the above are then fixed to the counter-surface by cold pressing or ultrasound welding.

4 Claims, 2 Drawing Sheets

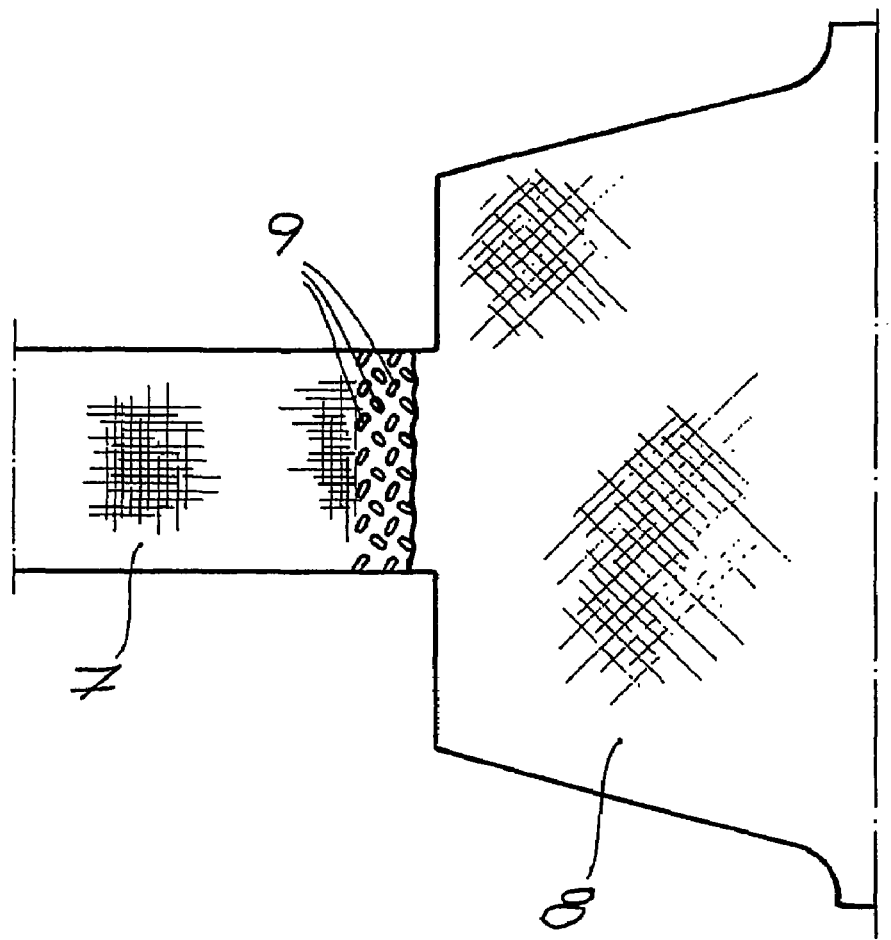

METHOD FOR THE APPLICATION OF REUSABLE FASTENERS ON DIAPERS

CROSS REFERENCE TO RELATED APPLICATIONS

Figure 1:
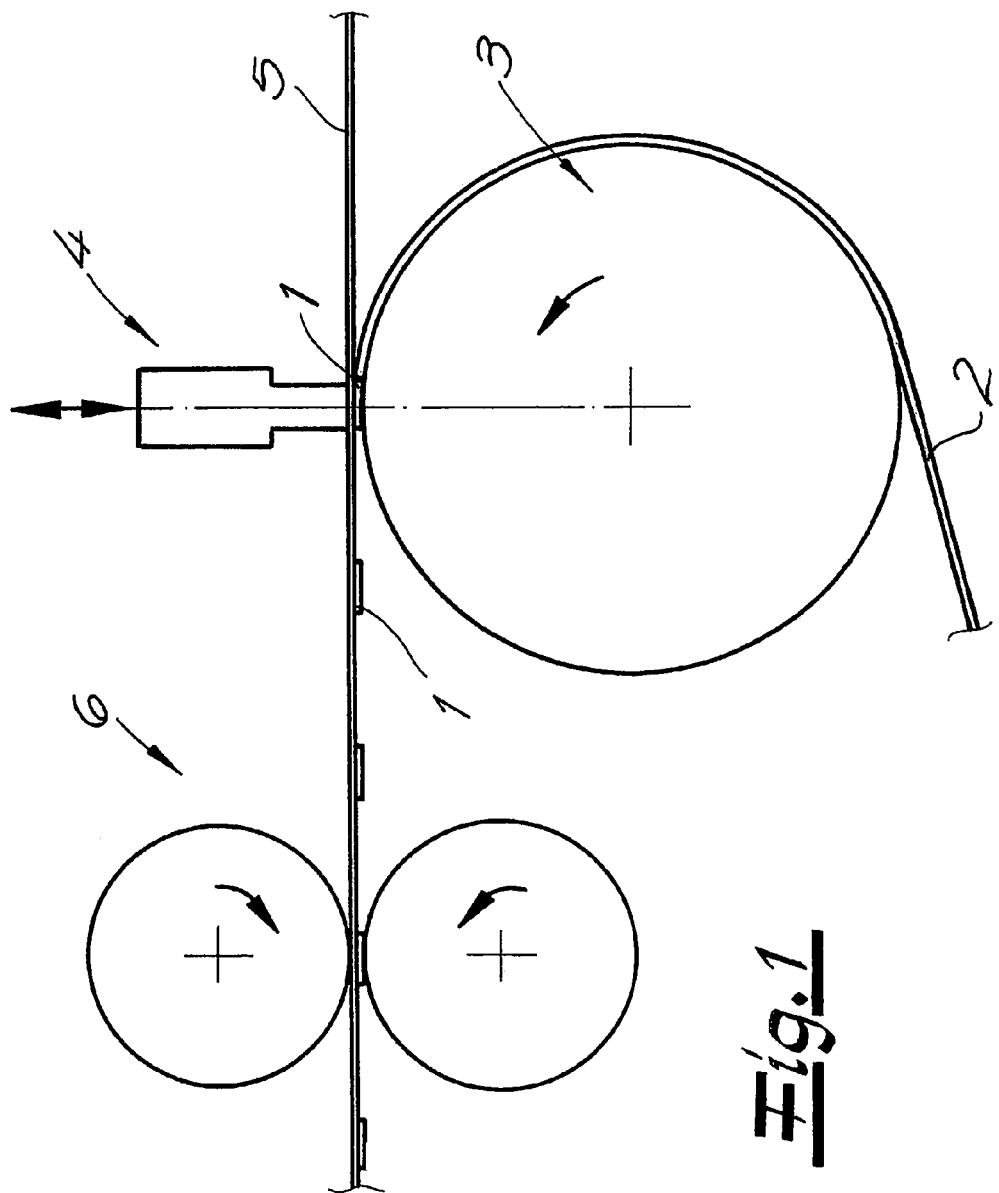

Applicant claims priority under 35 U.S.C. §119 of German Application No. 103 44 536.6 filed Sep. 25, 2003. Applicant also claims priority under 35 U.S.C. §365 of PCT/EP2004/010775 filed Sep. 24, 2004. The international application under PCT article 21(2) was not published in English.

The invention relates to a method for affixing a reusable fastener that consists of a fastener tape and a fastener strip to a baby diaper, whereby strips that consist of a carrier and a material laminated on, having fastener elements in the form of loops or hooks, are attached to the baby diaper without adhesive.

The material of the fastener band, i.e. fastener strip that can be laminated on can be produced by means of textile technology. The loops or hooks, which are produced by means of warp-knitting, for example, interact in the manner of a hook-and-loop system, whereby hook-shaped fastener elements of the one textile material engage into loops of the other textile material. The carrier of the fastener band and/or fastener strip can consist of a single-layer or multi-layer film, a textile material, or a laminate of a carrier film and a textile material laminated onto one side or both sides. Furthermore, the carrier can have a region having differing elasticity in the longitudinal direction of the strip. However, it is practical if at least the connection regions of the carrier, at which the bond with the baby diaper is produced, are configured as low-stretch regions. Polyolefins are particularly suitable as materials for the carrier of the fastener band and fastener strip.

Within the framework of the known measures, the fastener bands and the fastener strips are attached to the diaper by means of an adhesive that is applied to the back of the carrier. Attachment takes place on the outer skin of the diaper, or on a component that is configured as a diaper ear, for example (DE 199 40 185 A1). Handling of materials provided with an adhesive makes great demands on processing. In particular, it must be assured that the adhesive parts are either covered with release films during processing, or only come into contact with other materials, with the adhesive side, at the desired point in time. Because of these problems, it is proposed in DE 199 52 417 A1 to coat the strips with a parting layer that contains silicone, on the side of the fastener elements, which layer must be cured after coating. This method is complicated.

From DE 197 03 557 A1, it is known to attach fastener strips to the outside of a baby diaper using ultrasound bonding. As another possibility for the production of mechanical bonds, bonding by means of heat and/or pressure can be considered (EP 0 877 589 B1). Ultrasound bonding as well as bonding by means of heat and pressure are relatively slow attachment methods. The required dwell time for the production of a firm bond is clearly longer than the time required for contact gluing. Attachment of a strip forming a reusable fastener to baby diapers by means of heat and pressure therefore appears not to be very suitable for practice, and has not been able to establish itself.

The invention is based on the task of simplifying the attachment of the fastener bands and fastener strips on the baby diaper. The method is supposed to be able to be integrated into the diaper production, and is not allowed to impair the production speed of the diaper production.

This task is accomplished according to the invention, in the case of the method described initially, in that the strips are basted on in a first method step, by means of thermobonding or ultrasound bonding, and firmly bonded to the countersurface in a second method step, by means of cold pressing. The two method steps are carried out in spatially separate workstations.

In the case of thermobonding, bonding of the materials takes place using hot tools. In the case of ultrasound bonding, stamping dies that oscillate at high frequency are used, which produce friction heat. By means of local melting and flow processes, the materials to be bonded are merely fixed in place in a first method step. In a second method step, in a spatially separate workstation, the materials are subsequently firmly bonded by means of cold pressing. In a continuous diaper production, the two method steps can be carried out at the same time, in the separate workstations. By dividing the attachment method into two method steps, the dwell time that is required for applying and attaching the fastener strips and fastener bands in the case of a continuous diaper production can be reduced by up to 50%.

According to a preferred embodiment of the invention, the strips are cut from a material web, with a cut transverse to the web running direction, and passed to the first workstation by means of a transfer device, in which the strips are applied to a web from which the diapers or parts of the diapers are produced, and basted on by means of thermobonding or ultrasound bonding. A rotating transfer device can be used, in particular, as the transfer device, which passes the strips to the workstation with a rotational movement in the same direction as the running direction of the web. Afterwards, the web is passed through the second workstation, in which the strips are firmly bonded to the web.

Using the method according to the invention, bonds between strips and diapers can be produced, which consist of attachment points disposed densely next to one another.

In the following, the invention will be explained using a drawing that presents an exemplary embodiment merely as an example. The drawing schematically shows:

FIG. 1 a method for affixing a reusable fastener that consists of a fastener tape and a fastener strip to a baby diaper, FIG. 2 the method product produced according to the method described.

In the case of the method shown in FIG. 1, strips 1 are cut from the material web 2, with a cut crosswise to the running direction of the web, and passed to a first workstation 4 by means of a rotating transfer device 3. The strips 1 cut from the material web 2 consist of a carrier and a material laminated on, having fastener elements in the form of loops or hooks. In the first workstation 4, they are applied to a web 5 from which diapers or parts of diapers are produced, and basted on by means of thermobonding or ultrasound bonding. The bond produced in the first workstation 4 merely serves to fix the strips 1 in place on a surface that forms the outside of the diaper. Afterwards, the web is passed through a second workstation 6, in which the strips 1 are firmly bonded to the web 5 by means of cold pressing or ultrasound bonding.

The method product produced according to the method described is shown in FIG. 2. FIG. 2 schematically shows a detail of a baby diaper having a lateral fastener band 7, which is attached to a connection region of the diaper configured as a diaper ear 8, and works together with a fastener strip disposed on the outside of the diaper, not shown in the figure, as a hook-and-loop fastener. The fastener band 7 consists of a carrier and a material laminated on, having hook-shaped fastener elements that work together with loop-shaped fastener elements of the fastener strip attached to the outside of the diaper. The material that is laminated on can be produced by means of textile technology.

The carrier of the fastener band can consist of a single-layer or multi-layer film, a textile material, e.g. nonwoven or knitted fabric, or a laminate of a carrier film and a textile material laminated on, on one or both sides. The carrier can have regions having differing elasticity in the longitudinal direction of the strip. Preferably, the connection region of the carrier that is used for attaching the carrier to the baby diaper is configured as a low-stretch region.

The bond between strip and diaper that is produced according to the method described above consists of attachment points 9 disposed densely next to one another, which were produced by means of local melting and/or flow processes, with the application of pressure.

The fastener strip that consists of a carrier and a material laminated on, having female fastener elements in the form of loops, is also attached to the outside skin of the diaper without adhesive, in the manner described, whereby the fastener strip is only based on, in a first method step, by means of thermobonding, and is then firmly bonded to the counter-surface in a second method step, by means of cold pressing or ultrasound bonding.

The invention claimed is:

1. Method for affixing a reusable fastener that consists of a fastener tape and a fastener strip to a baby diaper, whereby strips that consist of a carrier and a material laminated on, having fastener elements in the form of loops or hooks, are cut from a material web with a cut crosswise to the running direction of the web and passed to a first workstation by means of a rotating transfer device, whereby in the first workstation the strips are applied without adhesive to a web from which diapers or part of diapers are produced and are basted on and merely fixed in place by means of local melting and flow processes by means of ultrasound bonding, whereby afterwards the web is passed through a spatially separate second workstation, in which the strips are firmly bonded to the web by means of cold pressing.

2. Method according to claim 1, wherein the strips are cut from a material web, with a cut transverse to the web running direction, and passed to the first workstation by means of a transfer device, in which the strips are applied to a web from which the diapers or parts of the diapers are produced, and basted on by means of thermobonding or ultrasound bonding, and that afterwards, the web is passed through the second workstation, in which the strips are firmly bonded to the web.

3. Method according to claim 2, wherein a rotating transfer device is used, which passes the strips to the workstation with a rotational movement in the same direction as the running direction of the web.

4. Method according to claim 1, wherein a bond is produced between strip and diaper, which consists of attachment points disposed densely next to one another.

* * * * *